United States Patent [19]

Nakano et al.

[11] Patent Number: 5,082,857

[45] Date of Patent: Jan. 21, 1992

[54] CHEMICAL COMPOUND

[75] Inventors: Hirofumi Nakano; Mitsunobu Hara; Yohichi Uosaki, all of Tokyo; Isao Kawamoto, Kanagawa; Keiiechi Takahashi; Katsushige Gomi, both of Shizuoka, all of Japan

[73] Assignee: Kyowa Hakko Kogyo Kabushiki Kaisha, Japan

[21] Appl. No.: 612,317

[22] Filed: Nov. 13, 1990

[30] Foreign Application Priority Data

Nov. 13, 1989 [JP] Japan .................. 1-294290

[51] Int. Cl.⁵ ..................... A61K 31/35; C07D 311/78
[52] U.S. Cl. ..................................... 514/453; 549/382
[58] Field of Search ................. 549/382, 384; 514/453

[56] References Cited

U.S. PATENT DOCUMENTS

| 4,847,387 | 7/1989 | Nakano et al. | 549/384 |
| 4,927,848 | 5/1990 | Konishi et al. | 514/453 |
| 4,954,641 | 9/1990 | Sato et al. | 549/384 |

OTHER PUBLICATIONS

CRC Handbook of Antibiotic Compounds, CRC Press (U.S.A. 1981), pp. 60–69, 166–173 & 315–317.
Amone et al., C.A., 84, 150,451w, 1976.

Primary Examiner—Nicky Chan
Attorney, Agent, or Firm—Schweitzer Cornman & Gross

[57] ABSTRACT

The present invention relates to a compound designated "DC114-C" having excellent anti-bacterial and anti-tumor activities. This compound may be obtained by fermentation of a microorganism of the genus Streptomyces, preferably Streptomyces sp. DO-114 (FERM BP-2641).

3 Claims, No Drawings

CHEMICAL COMPOUND

The present invention relates to a compound designated "DC114-C" hereinafter. DC114-C exhibits anti-bacterial and anti-tumour activity and may be useful as an anti-bacterial and anti-tumour agent.

Known antibiotic substances having the quinone skeleton and exhibiting anti-tumour activity of the known types are exemplified by various compounds of anthracycline-type and mitomycin-type [CRC Handbook of Antibiotic Compounds, CRC Press, U.S.A. (1981)].

The present inventors have however found that a microorganism which we have isolated from the soil of Ami-machi, Ibaraki-ken, Japan, is capable of producing a substance which is capable of exhibiting anti-bacterial and anti-tumour activity. This substance has been designated by us as DC114-C.

According to one aspect of the present invention, there is provided a compound DC114-C represented by the following formula:

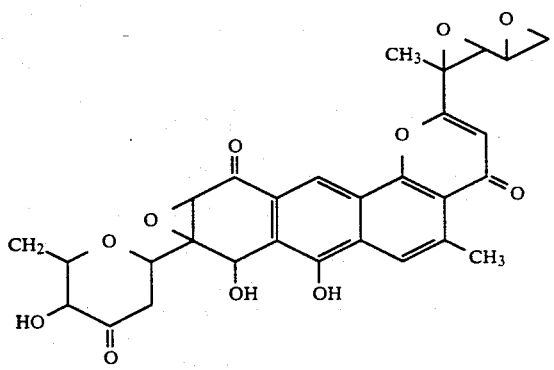

Compound DC114-C may be obtained by fermentation of a microorganism of the genus Streptomyces.

DC114-C has the following physico-chemical characteristics:

(1) Molecular weight: 550.
(2) Molecular formula: $C_{29}H_{26}O_{11}$.
(3) Mass analysis: SIMS 551 (M+1).
(4) Specific rotation: $[\alpha]_D^{26} = -66°$ (c=0.11, acetone).
(5) Ultraviolet absorption spectrum: in methanol $\lambda_{max}$: 218 nm ($\epsilon$=35.000), 274 nm ($\epsilon$=40.000), 370 nm (sh, $\epsilon$=9.300), 381 nm ($\epsilon$=12.000).
(6) Infrared absorption spectrum: (by KBr tablet method) (cm$^{-1}$) 3417, 1726, 1689, 1645, 1614, 1411, 1373, 1282, 1112.
(7) PMR spectrum: (measured in DMSO-d$_6$, using TMS as the internal standard).

$^1$H-NMR (500 MHz): δ (ppm) 10.40 (1H, br. s), 8.16 (1H, s), 7.70 (1H, br, s), 7.68 (1H, s), 6.40 (1H, s), 5.74 (1H, s), 5.47 (1H, d, J=7.3 Hz), 4.58 (1H, dd, J=11.8, 2.9 Hz), 4.51 (1H, dq, J=6.6, 6.5 Hz), 4.50 (1H, m), 3.97 (1H, s), 3.27 (1H, ddd, J=6.6, 4.4, 2.6 Hz), 3.19 (1H, d, J=6.6 Hz), 3.00 (1H, dd, J=13.4, 11.8 Hz), 2.96 (1H, dd, J=4.8, 4.4 Hz), 2.89 (1H, dd, J=4.8, 2.6 Hz), 2.783 (3H, s), 2.780 (1H, dd, J=13.4, 2.9 Hz), 1.89 (3H, s), 1.10 (3H, d, J=6.5 Hz).

(8) CMR spectrum: (measured in DMSO-d$_6$, using TMS as the internal standard) $^{13}$C-NMR (125 MHz): δ (ppm) 206.2, 192.2, 178.2, 163.8, 154.6, 152.2, 136.3, 128.0, 127.3, 122.0, 119.6, 119.5, 119.3, 112.1, 110.6, 75.3, 74.4, 66.5, 65.7, 64.5, 64.1, 57.2, 56.7, 48.6, 43.7, 43.0, 23.1, 14.3, 12.6.

(9) Solubility in various solvents: Readily soluble in chloroform, dimethylsulfoxide (DMSO), methanol, ethyl acetate and acetone. Hardly soluble in water and n-hexane.

(1)(0) Colour reaction: Positive in the p-anisidine and iodine reaction.

(1)(1) Colour and nature: Brownish acidic substance.

(1)(2) Thin layer chromatography: by using HPTLC plate Art. 15647, commercial product of Merck AG.

| Rf | Developer |
|---|---|
| 0.20 | toluene:acetone (2:1 v/v). |
| 0.30 | chloroform:methanol:acetic acid (20:1:1 v/v) |

The spot of DC114-C may be detected, for example, by the bioassay using *Bacillus subtilis*, hot sulfuric acid and ultraviolet absorption.

We have been unable to find any other compound in the literature having all the above-mentioned characteristics.

The biochemical characteristics of DC114-C are as follows:

(A) ANTI-BACTERIAL ACTIVITY

The following Table 1 indicates minimum inhibitory concentration (MIC) of DC114-C against selected microorganisms, measured by the agar dilution method at pH 7.0.

TABLE 1

| Test microorganism | MIC (μg/ml) of DC114-C |
|---|---|
| *Staphylococcus aureus* ATCC 6538P | 0.07 |
| *Enterococcus faecium* ATCC 10541 | 0.13 |
| *Bacillus subtilis* No. 10707 | 0.26 |
| *Klebsiella pneumoniae* ATCC 10031 | 4.2 |
| *Salmonella typhi* ATCC 9992 | 8.3 |

(B) GROWTH INHIBITION AGAINST BALB 3T3/H-RAS CELLS

Into each well of a 96 well microtitre plate was poured a Balb 3T3/H-ras cell suspension (each 0.1 ml), containing 2×10$^4$ cell/ml and prepared by suspending the cells in medium A. Medium A was prepared by adding to F10 medium (commercial product of Gibco) fetal calf serum (0.1 g/ml), penicillin (100 Unit/ml) and streptomycin (100 μg/ml).

On each occasion, the plate was incubated at a temperature of 37° C. for 20 hours in a carbon dioxide incubator. Then a test sample of DC114-C was suitably diluted with medium A. The diluted sample (0.05 ml) was added to each well, followed by incubation at a temperature of 37° C. for 72 hours in the incubator. After this, the supernatant was removed from the medium. Another medium (each 0.1 ml), prepared by adding to medium A neutral red (0.02%), was added to each well. The cells were dyed by incubation at a temperature of 37° C. for one hour in the incubator.

The supernatant was removed and the residue was washed once with physiological saline. After removal of the dyestuff by using a mixture of 0.001N hydrochloric acid and 30% ethanol, a micro-plate reader was applied to the material to measure the absorbance at 550 nm. The following Table 2 indicates the results obtained by comparing the absorbance of untreated cells with the absorbance of the test sample measured at various concentrations.

TABLE 2

| Test sample | IC$_{50}$ (μg/ml)*, 72 hours |
| --- | --- |
| DC114-C | 0.06 |

Note:-*concentration required for 50% inhibition of the growth of the cells

(C) ACUTE TOXICITY

The acute toxicity of Compound DC114-C in mice is 17.6 mg/kg by intravenous injection, in contrast to the corresponding value of 5.0 mg/kg for mitomycin C.

(D) CURING EFFECT ON SARCOMA 180 TUMOUR CELLS

As test animals, female mice of ddy strain (body weight about 20 g; each group consisting of 6 mice) were used. $5 \times 10^6$ Sarcoma 180 tumour cells were, on each occasion, inoculated into the animal under the skin of the armpit. From the first to 5th days after this, a dose of phosphate-buffered physiological saline (PBS; 0.2 ml) containing a given concentration of DC114-C as shown in Table 3 was intravenously given to the test animal. The administration was effected 5 times with an interval of 24 hours between each. For comparative purposes, 24 hours after inoculation, a PBS solution (0.2 ml) containing a given amount of mitomycin C was intravenously administered to other animals. 10 days after inoculation, T/C values viz. the ratio of the average volume (mm$^3$) of the tumours found on the animals treated with the test compounds to the corresponding volume found on the untreated animals were measured and these are shown in the following Table 3.

TABLE 3

| Test compound | Dose (mg/kg. each) | T/C |
| --- | --- | --- |
| DC114-C | 6.25 | 0.15 |
|  | 3.13 | 0.26 |
|  | 1.56 | 0.48 |
|  | 0.78 | 0.56 |
| Mitomycin C | 6.0 | 0.21 |
|  | 4.0 | 0.25 |
|  | 2.0 | 0.41 |

PREPARATION OF DC114-C

According to another aspect of the present invention, there is provided a process for the preparation of compound DC114-C, which comprises the steps of culturing a microorganism of the genus Streptomyces capable of producing compound DC114-C in a culture medium to accumulate the desired compound in the medium and recovering the same from the medium.

Any and all strains of the genus Streptomyces may be used for this process so far as they are capable of producing DC114-C, although it is also possible to use DC114-C-producing mutant strains thereof. Such mutant strains may be artificially mutated or naturally-occurring. Artificially mutated strains may be those produced by irradiation of ultraviolet rays or X-rays and may also be produced by using various mutagens.

Preferred examples of DC114-C-producing strain include strain Streptomyces sp. DO-114.

The mycological characteristics of strain DO-114 have been determined by the methods which were proposed by the International Streptomyces Project (ISP) to determine the characteristics of Streptomyces strains [E. B. Shirling and D. Gottlieb: Int. J. Syst. Bacteriol., 16, 313-340 (1966)]. The B. Becker et al. method [Appl. Microbiol., 12, 421-423 (1964)] has been used to assay isomers of diaminopimelic acid found in the hydrolyzate of the whole cells. Morphological studies of the cells were carried out by using an optical microscope; a scanning electron microscope was used, in particular, to study morphologically the surfaces of the spores. Colours were designated with reference to Color Harmony Manual, the 4th Edition (1958), published by Container Corporation of America.

The morphological characteristics of Streptomyces sp. DO-114 are as follows.

(1) Morphology:
Aerial mycelium: Branched.
Spore: In the form of a long chain comprising more than 10-30 conidia on aerial mycelium, the chain being curved or in the form of a loop.
Surface of spore: Smooth.
Motility of spore: Negative.
Form and size of spore: Oval (0.5×0.7 μm). Nucleus and sporangium are not observed.

(2) Colour tone:
Aerial mycelium: Gray to white.
Vegetative hypha: Gray.
Soluble pigment: Light yellow.
Melanoid pigment: Found. Brown.

(3) Chemical analysis of cell wall: Stereotype of diaminopimelic acid: LL type.

(4) Physiological characteristics: Assimilability of carbon sources:
Positive: Glucose, xylose, mannitol, arabinose, rhamnose, raffinose, lactose, sucrose, galactose.
Negative: inositol, salicin.

| | |
| --- | --- |
| Liquefication of gelatin:* | Negative |
| Hydrolysis of starch: | Positive |
| Coagulation of skimmed milk:* | Negative |
| Peptonization of skimmed milk:* | Positive |
| Decomposition of cellulose: | Positive |
| Growth temperature:** | 16-37° C. (optimum 28-32° C.) |

[Note:-Measured after culturing at 28° C. for 2 weeks except * after one month and ** after 2 days]

(5) Growth conditions on various agar media:
The strain was cultured at a temperature of 28° C. for 28 days on various agar media to give the results shown in the following Table 4.

TABLE 4

| Agar medium | Growth conditions |
| --- | --- |
| Sucrose-nitrate agar medium | G: good |
|  | AM: abundant, white (a) |
|  | SM: camel (3ie) |
|  | P: found, light yellow |
| Glucose-asparagin agar medium | G: normal |
|  | AM: abundant, cobalt gray (2fe) |
|  | SM: cobalt gray (2fe) to bisque (3ec) |
|  | P: not found |
| Glycerol-asparagin agar medium | G: good |
|  | AM: abundant, cobalt gray (2fe) |
|  | SM: toast ten (4lg) to natural (2dc) |
|  | P: not found |
| Starch agar medium | P: good |
|  | G: abundant, cobalt gray (2fe) |
|  | AM: bamboo (2gc) |
|  | SM: not found |
| Tyrosine agar medium | G: good |
|  | AM: abundant, cobalt gray (2fe) |
|  | SM: dark brown (2pn) |
|  | P: found, light yellow |
| Nutrient agar | G: good |

TABLE 4-continued

| Agar medium | Growth conditions |
|---|---|
| medium | AM: abundant, cobalt gray (2fe) |
|  | SM: camel (3ie) |
|  | P: not found |
| Yeast-malt agar | G: good |
| medium | AM: abundant, cobalt gray (2fe) |
|  | SM: golden brown (3pi) to yellow maple (3ng) |
|  | P: found, yellow |
| Oatmeal agar | G: good |
| medium | AM: abundant, dark cobalt gray (2ih) |
|  | SM: light brown (31g) |
|  | P: found, brown |
| Peptone-yeast | G: good |
| extract-iron agar | AM: not found |
| medium | SM: camel (3ie) |
|  | P: found, brown |

Notes:-
G: Growth degree
AM: Formation and colour tone of aerial mycelium
SM: Colour tone of vegetative hypha
P: Colour tone of soluble pigment (6) Identification of strain DO-114:

With respect to the fact that diaminopimelic acid of LL-type is present in the cell wall of DO-114 strain and with reference to the classification of strains of Actinomycetes according to M. P. Lechvalier and H. A. Lechvalier, this strain may be classified into Cell wall I type.

In view of such classification and morphological characteristics, it is reasonable to classify this strain into the genus Streptomyces.

In the light of the characterizing features of this strain such as the aerial mycelium coloured gray to white, spore chains in the form of curves or loops, smooth surface of spore, productivity of melanoid pigment and assimilability of carbon sources and with reference to the reports by the ISP [Int. J. Syst. Bacteriol. 18, 69–189 (1968); ibid., 18, 279–392 (1968); ibid., 19, 391–512 (1969); ibid., 22, 265–394 (1972)] and to Bergey's Manual of Determinative Bacteriology, 8th Edition, edited by R. E. Buchanan and N. E. Gibbons, various species recognized by a learned society [V. B. D. Skerman et al., Int. J. Syst. Bacteriol., 30, 225–420 (1980)] have been studied to discover a species whose characteristics are taxonomically similar to the characteristics of the present strain.

As a result, it was impossible to specify the species of the present strain, even though the present strain is somewhat close to *Streptomyces galiaeus*. Thus, the present strain was named as Streptomyces sp. DO-114. This microorganism was deposited with the Fermentation Research Institute, Agency of Industrial Science and Technology, Japan (FRI) on Nov. 8, 1989 under the Budapest Treaty, the deposition number being FERM BP-2641.

Microorganisms capable of producing DC114-C may be cultured in conventional manner which may be applicable to various microorganisms of Actinomycetes, by using any or all organic and synthetic culture media so far as they contain suitable amounts of assimilable carbon source, nitrogen and inorganic substances as well as substances required for the growth and promotion of the productivity of compound DC114-C.

Examples of carbon sources which may be used for this purpose include glucose, starch, dextrin, mannose, fructose, sucrose, lactose, xylose, arabinose, mannitol and molasses, which may be used solely or in combination. If desired, hydrocarbons, alcohols and organic acids may also be used, depending upon the assimilability of the microorganism used.

Examples of nitrogen sources which may be used for the process of the present invention include ammonium chloride, ammonium sulfate, ammonium nitrate, sodium nitrate, urea, peptone, meat extract, yeast extract, dried yeast, corn steep liquor, soyabean powder and cazamino acid, which may be used solely or in combination. If desired, for example, sodium chloride, potassium chloride, magnesium sulfate, calcium carbonate, potassium dihydrogen phosphate, dipotassium hydrogen phosphate, ferrous sulfate, calcium chloride, magnesium sulfate, zinc sulfate, copper sulfate and other inorganic salts may be added to the medium. It is also possible to add to the medium traceable amounts of substances which promote the growth and the productivity of DC114-C.

For culturing, the use of liquid media, particularly with deep stirring is preferred. Usually, culturing may be effected at a temperature of 16°–37° C., preferably, 25°–32° C. and at a pH of 4–10, preferably 6–8 and may be completed in a period of 1–7 days to accumulate the desired compound DC114-C in the cultured liquor and the microbial cells. The pH of the medium may be adjusted by using, for example, ammonia water and a solution of ammonium carbonate. The fermentation is discontinued at the time the accumulated amount of the desired substance reaches the maximum.

Isolation of DC114-C from the cultured matter and its purification may be effected in conventional manner which is applicable to isolate and purify various metabolic products derived from microorganisms.

Thus, for example, the cultured matter is filtered to divide it into the filtrate and microbial cells. The cells are extracted, for example, with chloroform or acetone. The extracted solution is combined with the filtrate. The combined solutions are then passed through a column packed with a polystyrene-type adsorbing resin such as, for example, Diaion HP20 (commercial product of Mitsubishi Kasei K. K., Japan) to adsorb the active substance onto the resin, which is then eluted by using, for example, ethyl acetate and acetone. The eluate is concentrated and subjected to, for example, silica gel column chromatography and high performance liquid chromatography to obtain DC114-C in the form of brown powders. In the course of culturing and purification, the behavior of DC114-C may be traced by means of, for example, the bioassay using *Bacillus subtilis* No. 10707 and the absorption of ultraviolet rays by thin layer chromatography of DC114-C.

According to a further feature of the present invention, we provide a pharmaceutical composition which comprises DC114-C as hereinbefore defined in admixture with a pharmaceutically acceptable carrier, diluent or excipient. The carrier diluent or excipient include those which are commonly used with anti-bacterial and/or anti-tumour agents.

The following non-limiting example illustrates the present invention.

EXAMPLE

Streptomyces sp. DO-114 (FERM-BP 2641) was used as a seed. The seed was cultured with shaking (200 r.p.m.) at a temperature of 30° C. for 48 hours by using a seed medium (300 ml) put in an Erlenmeyer flask (capacity 2 l), the seed medium being composed of 5 g/l of Bacto Tryptone (commercial product of Difco.), 5 g/l of yeast extract, 3 g/l of meat extract, 10 g/l of soluble starch, 10 g/l of glucose and 5 g/l of calcium carbonate [pH 7.2 before sterlization].

The resultant seed culture was transferred to a main medium (15 l) put in a 30 l fermentor at a ratio of 10% by volume for culturing with aeration (15 l per min.) and shaken (200 r.p.m.) for 80 hours at a temperature of 28° C. The composition of the main medium was as follows: glycerol 25 g/l; glucose 25 g/l; dried yeast 15 g/l; $KH_2PO_4$ 0.5 g/l; $MgSO_4.7H_2O$ 0.5 g/l; calcium carbonate 5 g/l.

The pH of the main medium was adjusted to 7.0 by using NaOH before sterilization, but was not adjusted during the culturing.

After completion of fermentation, n-propanol (15 l) was added to the cultured broth whilst shaking it. The cultured broth was then filtered to separate the cells from the precipitates. The resultant filtrate (28 l) was concentrated. After dilution with water, the solution was passed through a column (10 l) packed with a polystyrene-type resin (Diaion HP20, commercial product of Mitsubishi Kasei K. K., Japan) to adsorb the active substance onto the resin. After eluting the column with deionized water and 50% methanol to remove undesired impurities, ethyl acetate was applied to the column to elute the active substance. The active fraction was concentrated and water was added to the concentrated solution, from which the active material was extracted using ethyl acetate. After removal of water content by applying sodium sulfate, the extract was concentrated and transferred to a silica gel column (BW300, commercial product of Fuji-Devison Kagaku K. K., Japan). Development was effected using a mixed solution of toluene:acetone (2:1 v/v). By concentrating the resultant eluate, there was obtained DC114-C in the form of brown powders (30 mg), having the physico-chemical and biological characteristics as described hereinbefore.

We claim:

1. A compound of formula:

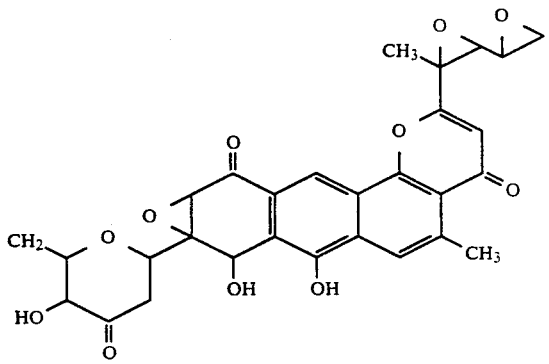

2. The compound of claim 1 obtained by the steps of culturing Streptomyces sp. DO-114 in a culture media to accumulate said compound and recovering said compound from the media.

3. A pharmaceutical composition comprising a compound as defined in claim 1 in admixture with a pharmaceutically acceptable carrier, excipient or diluent.

* * * * *